(12) United States Patent
Weening et al.

(10) Patent No.: US 11,033,651 B2
(45) Date of Patent: Jun. 15, 2021

(54) SYSTEM AND METHOD OF CONTROLLING OPERATION OF A LIQUID DIFFUSION APPLIANCE

(71) Applicant: Prolitec, Inc., Milwaukee, WI (US)

(72) Inventors: Richard Weening, Seattle, WA (US); Marc Robert, Mukwanago, WI (US)

(73) Assignee: PROLITEC INC., Milwaukee, WI (US)

( * ) Notice: Subject to any disclaimer, the term of this patent is extended or adjusted under 35 U.S.C. 154(b) by 333 days.

(21) Appl. No.: 15/346,276

(22) Filed: Nov. 8, 2016

(65) Prior Publication Data

US 2017/0049920 A1 Feb. 23, 2017

Related U.S. Application Data

(63) Continuation of application No. 14/678,720, filed on Apr. 3, 2015, now abandoned, which is a continuation of application No. 13/090,240, filed on Apr. 19, 2011, now abandoned, which is a continuation-in-part of application No. 11/691,363, filed on Mar. 26, 2007, now Pat. No. 7,930,068.

(51) Int. Cl.
*A61L 9/12* (2006.01)
*A61L 9/14* (2006.01)
*F24F 8/50* (2021.01)

(52) U.S. Cl.
CPC .................. *A61L 9/122* (2013.01); *A61L 9/14* (2013.01); *A61L 2209/111* (2013.01); *F24F 8/50* (2021.01)

(58) Field of Classification Search
None
See application file for complete search history.

(56) References Cited

U.S. PATENT DOCUMENTS

| 2,591,134 A | 4/1952 | Canaris |
| 5,924,597 A | 7/1999 | Lynn |

(Continued)

FOREIGN PATENT DOCUMENTS

| EP | 0 345 149 A2 | 12/1989 |
| EP | 1609128 A1 | 12/2005 |

(Continued)

OTHER PUBLICATIONS

Baseline-mocon, Inc., "VCO.Traq: USB Toxic Gas Detector & Data Logger," Product Data Sheet, Feb. 3, 2012, 2 pages.

*Primary Examiner* — Sean Schechtman
(74) *Attorney, Agent, or Firm* — Seed IP Law Group LLP

(57) ABSTRACT

A method of maintaining a desired level of a dispersed liquid within an occupiable semi-enclosed space is provided. The method includes: providing a liquid diffusion appliance including a liquid to be dispersed; operating the liquid diffusion appliance to disperse the liquid into the occupiable semi-enclosed space throughout a treatment period in which the occupiable space is subjected to entry and exit of occupants to and from the occupiable semi-enclosed space; sensing the concentration of one or more chemical components of the dispersed liquid within the occupiable semi-enclosed space; and modifying the operation of the liquid diffusion appliance based on the concentration of the one or more chemical components of the dispersed liquid within the occupiable semi-enclosed space to achieve a desired concentration.

13 Claims, 10 Drawing Sheets

(56) References Cited

U.S. PATENT DOCUMENTS

| | | | |
|---|---|---|---|
| 6,267,297 B1 | 7/2001 | Contadini et al. |
| 6,400,996 B1 | 6/2002 | Hoffberg et al. |
| 6,712,287 B1 | 3/2004 | Le Pesant et al. |
| 6,739,479 B2 | 5/2004 | Contadini et al. |
| 6,790,011 B1 | 9/2004 | Le Pesant et al. |
| 6,909,972 B2 | 6/2005 | Centanni |
| 7,326,382 B2 | 2/2008 | Adiga et al. |
| 7,651,077 B1 | 1/2010 | Rosener et al. |
| 7,850,931 B2 | 12/2010 | McDonell et al. |
| 7,930,068 B2 | 4/2011 | Robert et al. |
| 8,855,827 B2 | 10/2014 | Weening et al. |
| 2003/0006899 A1 | 1/2003 | Najmi et al. |
| 2003/0175148 A1 | 9/2003 | Kvietok et al. |
| 2004/0050951 A1 | 3/2004 | Almero |
| 2004/0050963 A1 | 3/2004 | Ray et al. |
| 2004/0184950 A1 | 9/2004 | McVey et al. |
| 2004/0187950 A1 | 9/2004 | Cohen et al. |
| 2005/0084415 A1 | 4/2005 | McVey et al. |
| 2005/0123436 A1 | 6/2005 | Cumberland |
| 2006/0060990 A1 | 3/2006 | Szpekman |
| 2006/0078461 A1 | 4/2006 | Kaplan |
| 2006/0117769 A1 | 6/2006 | Helt et al. |
| 2006/0140817 A1 | 6/2006 | Cumberland et al. |
| 2006/0226787 A1 | 10/2006 | Krichtafovitch et al. |
| 2006/0237090 A1 | 10/2006 | Benalikhoudja |
| 2006/0261188 A1* | 11/2006 | Ito .................. A61L 9/14 |
| | | 239/306 |
| 2007/0082601 A1 | 4/2007 | Desrochers et al. |
| 2007/0166185 A1 | 7/2007 | Bartels |
| 2010/0070086 A1 | 3/2010 | Harrod et al. |
| 2010/0143186 A1 | 6/2010 | Belmonte et al. |
| 2011/0253797 A1 | 10/2011 | Weening et al. |
| 2012/0097753 A1 | 4/2012 | Kelly et al. |
| 2018/0093006 A1 | 4/2018 | Kelly et al. |

FOREIGN PATENT DOCUMENTS

| | | |
|---|---|---|
| FR | 96/23530 | 8/1996 |
| JP | 2005-524522 A | 8/2005 |
| WO | 90/12600 A1 | 11/1990 |
| WO | 96/23530 A1 | 8/1996 |
| WO | 2004/080604 A2 | 9/2004 |

* cited by examiner

| ROOM VOL (cft) | DIAL (DS) | NSU OUTPUT (mL/hr) | SPEED (%PWM) | TON (sec) | TON (mn) | TOFF (sec) | TOFF (mn) | DUTY CYCLE (% on) | AVG CONSUMP (mL/hr) | MONTHLY USAGE (mL) | CARTRIDGE LIFE (weeks) |
|---|---|---|---|---|---|---|---|---|---|---|---|
| 80 | 1 | | | | | | | | | | 150 |
| 160 | 2 | | | | | | | | | | 102 |
| 240 | 3 | | | | | | | | | | 80 |
| 320 | 4 | | | | | | | | | | 66 |
| 400 | 5 | | | | | | | | | | 56 |
| 480 | 6 | | | | | | | | | | 49 |
| 560 | 7 | | | | | | | | | | 35 |
| 640 | 8 | | | | | | | | | | 31 |
| 720 | 9 | | | | | | | | | | 28 |
| 880 | 10 | | | | | | | | | | 26 |
| 1040 | 11 | | | | | | | | | | 24 |
| 1200 | 12 | | | | | | | | | | 22 |
| 1360 | 13 | | | | | | | | | | 20 |
| 1710 | 14 | | | | | | | | | | 16 |
| 1890 | 15 | | | | | | | | | | 15 |
| 2070 | 16 | | | | | | | | | | 14 |
| 2250 | 17 | | | | | | | | | | 13 |
| 2430 | 18 | | | | | | | | | | 13 |
| 2610 | 19 | | | | | | | | | | 12 |
| 2880 | 20 | | | | | | | | | | 11 |
| 3060 | 21 | | | | | | | | | | 9.5 |
| 3240 | 22 | | | | | | | | | | 9.1 |
| 3420 | 23 | | | | | | | | | | 8.7 |
| 3630 | 24 | | | | | | | | | | 8.4 |
| 3780 | 25 | | | | | | | | | | 8.0 |
| 3960 | 26 | | | | | | | | | | 7.7 |
| 4140 | 27 | | | | | | | | | | 7.5 |
| 4320 | 28 | | | | | | | | | | 6.4 |
| 4500 | 29 | | | | | | | | | | 6.2 |
| 4680 | 30 | | | | | | | | | | 6.0 |
| 4950 | 31 | | | | | | | | | | 5.8 |
| 5130 | 32 | | | | | | | | | | 5.6 |
| 5310 | 33 | | | | | | | | | | 5.5 |
| 5490 | 34 | | | | | | | | | | 5.3 |
| 5670 | 35 | | | | | | | | | | 4.6 |
| 5850 | 36 | | | | | | | | | | 4.5 |
| 6030 | 37 | | | | | | | | | | 4.4 |
| 6930 | 38 | | | | | | | | | | 4.2 |
| 7100 | 39 | | | | | | | | | | 4.1 |
| 7300 | 40 | | | | | | | | | | 4.0 |
| 7500 | 41 | | | | | | | | | | 4.0 |
| | 42 | | | | | | | 100.0% | | | 2.2 |
| | 43 | | | | | | | 100.0% | | | 1.8 |
| | 44 | | | | | | | 100.0% | | | 1.5 |
| | 45 | | | | | | | 100.0% | | | 1.3 |
| | 46 | | | | | | | 100.0% | | | 1.1 |
| | 47 | | | | | | | 100.0% | | | 1.0 |

FIG. 4

SYSTEM AND METHOD OF CONTROLLING OPERATION OF A LIQUID DIFFUSION APPLIANCE

CROSS-REFERENCE TO RELATED APPLICATION

The present application is a continuation of U.S. patent application Ser. No. 14/678,720, filed Apr. 3, 2015, which is a continuation of U.S. patent application Ser. No. 13/090,240, filed Apr. 19, 2011, which is a continuation-in-part of commonly-owned U.S. patent application Ser. No. 11/691,363, filed on Mar. 26, 2007, the disclosure of which is incorporated herein by reference in its entirety.

BACKGROUND

Technical Field

The present disclosure relates generally to systems and methods of controlling operation of a liquid diffusion device.

Description of the Related Art

In existing scent and liquid diffusion devices, a variety of approaches to controlling the operation or output of the devices are currently used. However, these conventional approaches tend to be sub-optimal with regard to initiating treatment of a space with a liquid or scent compound, and do not take into account fatigue or resistance by users or occupiers of the space. Existing approaches also do not take into account operational characteristics of the diffusion devices in determining when, for how long and at what speed to operate the apparatus.

Conventional controls for dispersal of liquid within a space may include sensors at locations spaced-apart from the diffusion device. However, providing connectivity between the sensor and the diffusion device may add undesirable complexity to an installation and may not be appropriate in situations where permanent or persistent mounting of the diffusion device is not desired or possible.

With liquid diffusion devices that are configured to disperse very small particles of liquid, for example, in the micron or sub-micron size range, it may be desirable to allow previously dispersed particles to decay or be removed from the air within a treated space before adding more particles to the space. If the rate of diffusion within the space is greater than the rate of decay, the concentration of the liquid within the treated space will trend upwards instead of remaining within a desired range of concentration.

Improvements to the conventional approaches to control and operation of liquid diffusion devices are desirable.

BRIEF SUMMARY

The present invention relates generally to systems and methods of controlling operation of a liquid diffusion device. In particular, the present invention relates to approaches to controlling speed and duration of the operation of a diffusion appliance and when the diffusion appliance should be operated.

BRIEF DESCRIPTION OF THE SEVERAL VIEWS OF THE DRAWINGS

The accompanying drawing figures, which are incorporated in and constitute a part of the description, illustrate several aspects of the invention and together with the description, serve to explain the principles of the invention. A brief description of the figures is as follows:

FIG. 4 is a chart illustrating operational characteristics of control schemes for diffusing a liquid by a liquid diffusion appliance according to the present disclosure.

DETAILED DESCRIPTION

Reference will now be made in detail to exemplary aspects of the present invention which are illustrated in the accompanying drawings. Wherever possible, the same reference numbers will be used throughout the drawings to refer to the same or like parts.

Figure 1:
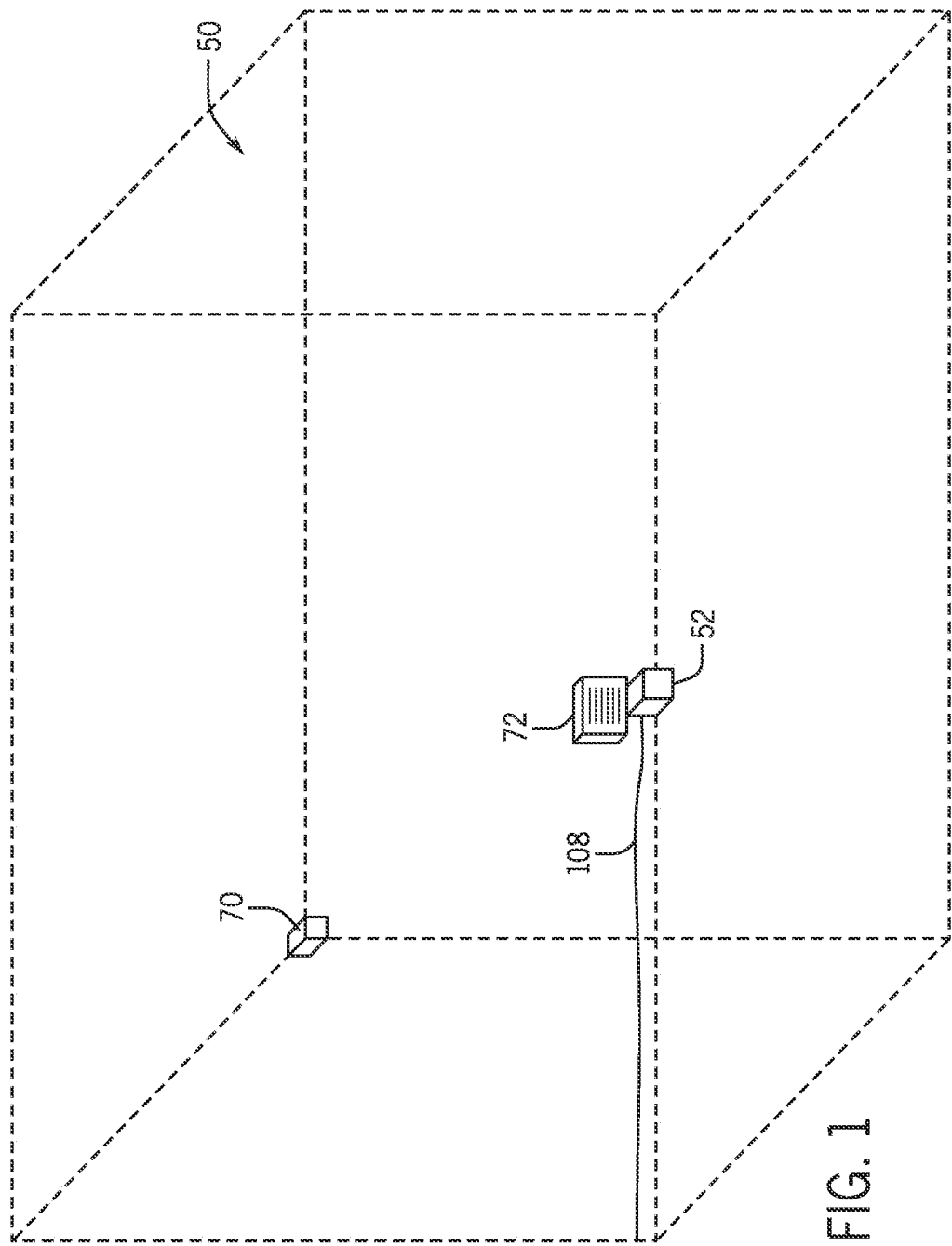
FIG. 1 is a diagrammatic view of a space to be treated by a diffused liquid and a liquid diffusion appliance positioned within the space.

FIG. 1 illustrates a space or room 50 into which it is desired to disperse a liquid for treating the air or other objects within space 50 and an appliance 52 configured to disperse such a liquid. Space 50 is preferably at least semi-enclosed, so that the treatment liquid may be retained within the space to have the desired effect. A completely sealed space is not necessary and it is anticipated that spaces with open entrances and exits may be suitable for treatment according to the present disclosure. For example, a hotel lobby, a building foyer, and a casino floor may have entrances and exits for people accessing the space and may be treated according to the present disclosure. An open air pavilion or an outdoor stadium may be examples of less suitable spaces for treatment according to the present disclosure, as the turnover or exchange of the atmosphere within the space may not permit adequate dwell time for the treatment liquid to accomplish the desired treatment goals. However, it is anticipated that certain types of liquid and treatment regimens may permit use of an appliance according to the present disclosure in these spaces.

While appliance 52 is shown within space 50, it is anticipated that the appliance need not be physically located within the space. It is necessary that appliance 52 be in fluid communication with space 50 to achieve the treatment of space 50 with airborne diffused liquids, as described herein.

Figure 2:
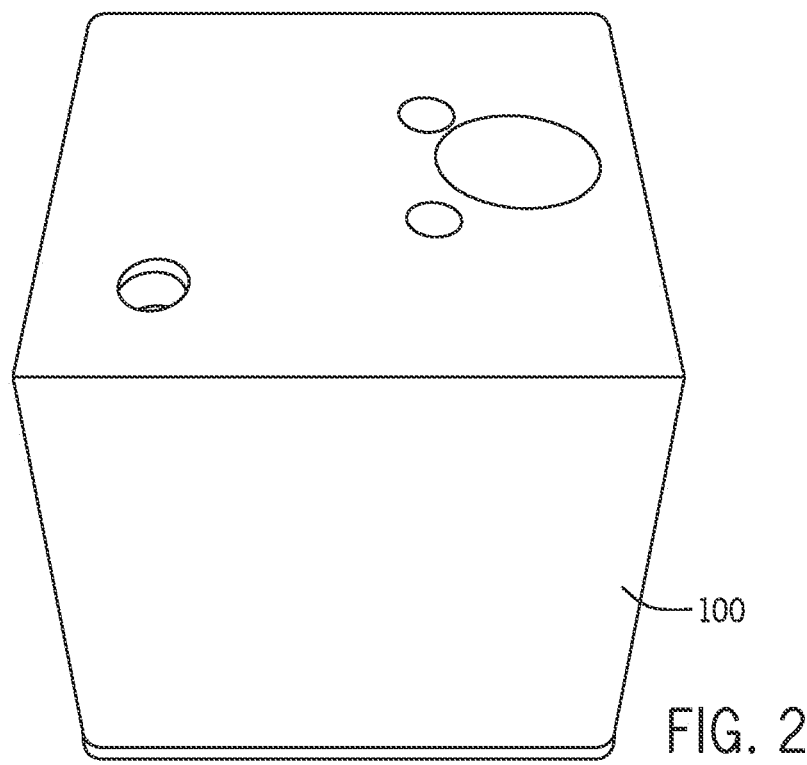
FIG. 2 is a perspective view of a liquid diffusion appliance according to the present disclosure.
Figure 2A:
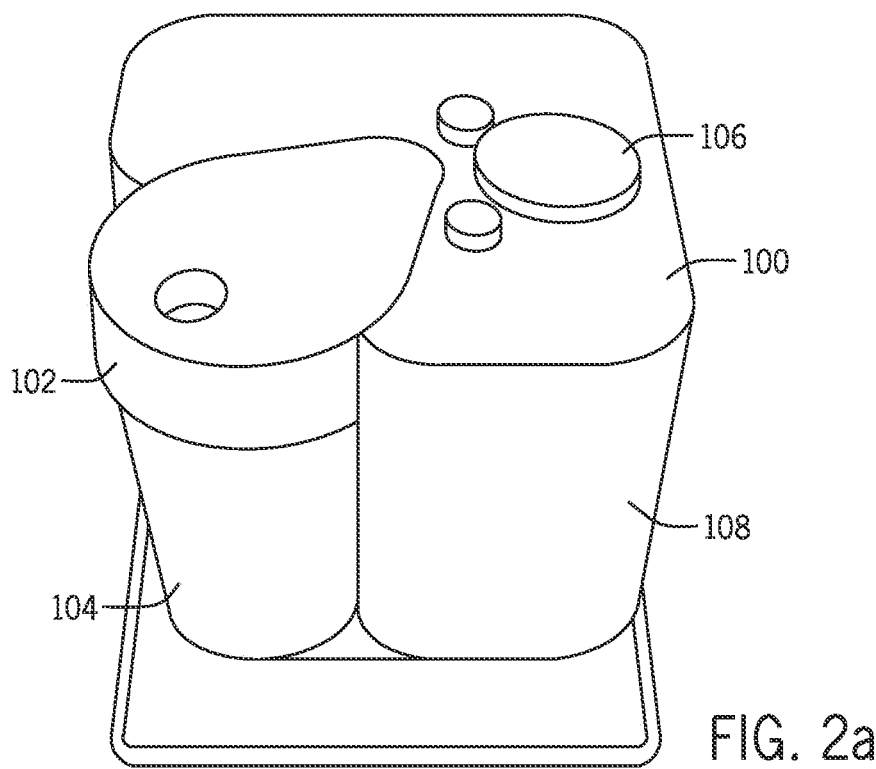
FIG. 2a is a perspective view of the liquid diffusion appliance of FIG. 2 with a cover removed.

FIGS. 2 and 2*a* illustrate a liquid diffusion appliance 100 according to the present disclosure with a cartridge 102 for holding a liquid 104 to be diffused or dispersed within an enclosed space. Appliance 100 may also include a controller 106 which may be mounted on-board or integrated into appliance 100 as shown. Alternatively, controller 106 may be mounted near to or on an exterior of appliance 100 but not incorporated into appliance 100. As a further alternative, controller 106 could be remotely located and connected to appliance 100 permitting remote control and operation of appliance 100. It is anticipated that more than one appliance may be controlled by the same controller 106 and that the multiple appliances may be mounted in the same or different spaces to be treated.

Figure 3:
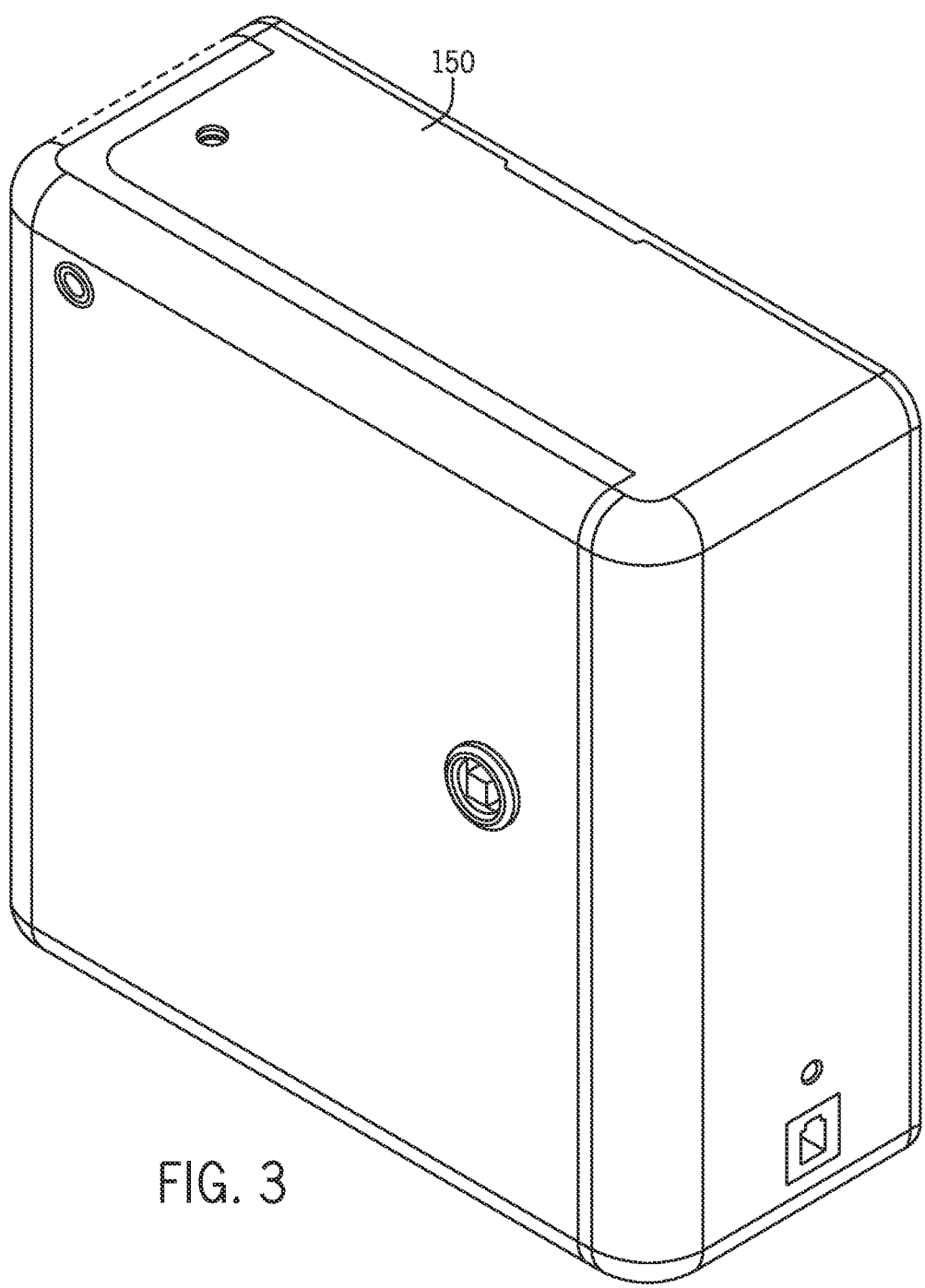
FIG. 3 is a perspective view of an alternative embodiment of a liquid diffusion appliance according to the present disclosure.
Figure 3A:
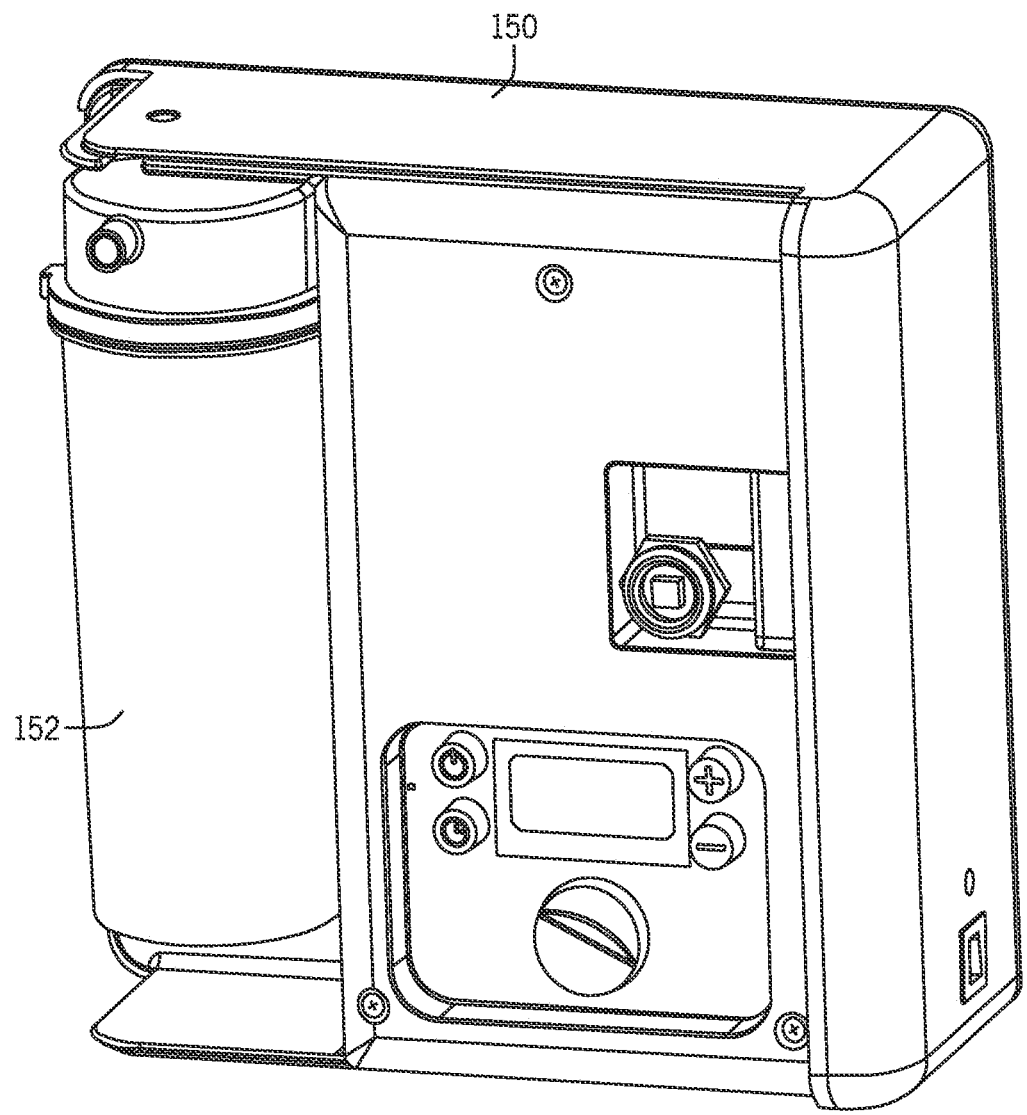
FIG. 3a is a perspective view of the liquid diffusion appliance of FIG. 3, with a front cover removed.

FIGS. 3 and 3*a* illustrate an alternative embodiment of a liquid diffusion appliance 150 according to the present disclosure with a cartridge 152 for holding liquid 104 to be diffused or dispersed within an enclosed space. Appliance 150 is similar in operation and function to appliance 100. In the following discussion of elements of appliance 100, it is intended that where appropriate the same discussion may be applied to appliance 150.

A source 108 of pressurized gas may also be provided within appliance 100. Source 108 may be an on-board compressor, as shown in FIG. 3, or may be a connection to an external compressor or other mechanical gas pressurizing device, as indicated by a gas conduit 54 in FIG. 1. Source 108 may also be a pre-compressed source which needs to be periodically refilled or recharged to a desired pressure.

As is known in conventional liquid diffusion devices, the pressurized gas may serve to draw liquid 104 into a venturi and then separate liquid 104 into smaller particles suitable for airborne dispersion out of appliance 100 into the space to be treated.

Liquid 104 may be a scent to provide a particularly desired odor within the space, such as a pleasing smell in a crowded administrative area. Such odors or scents may be selected from aromatherapy selections to encourage desirable responses among the users of the space to be treated or based on other desired atmospheric conditioning.

Alternatively, liquid 104 may be selected from one of a variety of known aerosol disinfectants or other bio-technical treatment options for providing a desired biological response within the space. Examples of this may be a disinfectant to clear or treat an area of known or suspected pathogens.

Regardless of the nature of the liquid being dispersed within a space, and purpose for which the liquid is being dispersed, for the purposes of this disclosure, it will be assumed that there is a desired density of the liquid to be achieved within the space. This desired density may also be a range of densities, based on the effect sought within the space.

Within appliance 100, cartridge 102 may incorporate a diffusion means such as a venturi in fluid communication with liquid 104 and through which pressurized gas from source 108 is configured to flow. Flow of gas through the venturi creates a vacuum to draw liquid 104 into the venturi and propel the diffused liquid from the venturi and out of appliance 100 into space 50. Alternatively, the diffusion means may be a separate component within or mounted adjacent to appliance 100 and not incorporated directly into cartridge 102. It is anticipated that other diffusion means may be used to separate liquid 104 into suitably small particles and disperse the particles into space 50. Preferably, the particle size generated by appliance 100 will be approximately in the micron range or smaller. Particles in this size range tend to remain is suspension within the air of the enclosed space until they contact an object, to which they then adhere. The rate of exchange of the air within the treated space will also have an impact on the dwell time that these micron or sub-micron sized particles of liquid have within the enclosed space to be treated.

FIG. 4 illustrates a chart of settings to control the operation of appliance 100 to disperse a desired amount of liquid 104 into space 50. Each horizontal line in the chart represents a control scheme 110 for controlling the operation of appliance 100, defining timing of operation of the diffusion means within the appliance and a flow rate of liquid 104 into the diffusion means and into space 50. Each control scheme may, for example, be associated with a particular numerical dial setting or other selectable setting 111 of controller 106, and in turn, each setting 111 may be defined as suitable for a particular volume 54 of space 50 in which appliance 100 is placed. A standard association of settings 111 to room size or volume 54 may be maintained if the characteristics of liquid 104 are kept consistent despite any different scents or other effects associated with the liquid. If this is done, then for any given room size and for any given liquid, the same setting of controller 106 can be used and liquids may be changed without the need to adjust controller 106.

Alternatively, an equivalents table may be supplied with a cartridge 102 including a liquid 104 which has significantly different characteristics from a standard or normal liquid. Such a table might be used to provide revised space volumes 54 associated with the respective settings 111 of controller 106. In the chart of FIG. 4, a total of forty-eight control schemes 110 associated with forty-eight distinct settings 111 of controller 106 are shown. More or fewer settings and/or control schemes 110 may be provided in such a chart or in controller 106 within the scope of the present disclosure.

For each control scheme 110, a speed setting 112 sets the rate of liquid flow through the appliance when the diffusion means is operating. A time on duration 114 and a time off duration 116 are combined to derive a duty cycle 118, which is the percentage of time that the diffusion means is operating. In most installations, it may be desirable to not have the diffusion means constantly operating, so that the duty cycle 118 may preferably be less than one. Based on the rate of exchange in the enclosed space, it may be desirable to have the appliance cycle on and off to permit particles already dispersed within the space to decay. Only when the rate of dispersion (based on the speed and timing of operation of appliance 100) is balanced with the rate of decay can the concentration of particles within the enclosed space be controlled within desired limits. One approach to balancing the dispersion and decay is to cycle the operation of appliance 100 on and off, as indicated in FIG. 4.

An added benefit of cycling operation of appliance 100 on and off, the concentration of liquid within the enclosed space may be allowed to fluctuate within a range of concentrations. Such a fluctuation may aid in the prevention of scent fatigue or olfactory adaptation that may deaden the ability of persons within the space to perceive the desired effect of the liquid diffused.

It may also be desirable to have a flow rate for each scheme be neither close to the maximum possible flow rate nor close to the minimum flow rate. The speed setting 112 is shown as a percentage of maximum for the diffusion means. Speed setting 112 may be kept within a range of values that corresponds to a preferred or optimal range of values for the operational characteristics of a particular diffusion means. For example, if the diffusion means works most efficiently between 40% and 65% of maximum operational speed, speed setting may be limited to values in this range. For a diffusion means that incorporates a venturi, the flow rate of the liquid may be directly related to the speed or volume of gas that is fed from source 108 through the venturi. In the chart of FIG. 4, the speed setting is expressed as a percentage of the maximum flow available from gas source 108.

Within the different control schemes 110 of FIG. 4, a stepwise approach may be indicated in the setting of flow rate or speed. For example, a first group of speed settings from control schemes 110 numbered from 1 to 6, may include the same speed setting 112 corresponding to a desired percentage of maximum gas flow rate. To accommodate different space volumes with the different schemes, the duty cycle for the different schemes may be changed. A higher percentage of time-on duration at the same flow rate or speed setting will permit treatment of a larger volume space before the flow rate needs to be altered. In the example of control schemes 1 to 6, treatment of spaces from 80 cubic feet up to 480 cubic feet may be accomplished with the same flow rate and different duty cycles.

Note that control schemes 42 to 47 include duty cycles of 100% and then vary the flow rate. These settings are for situations where continuous diffusion of liquid 104 is desired or required or when diffusion is controlled along with the air room ventilation rate. As can be seen in a column 120 labeled Cartridge Life, there is a distinctly greater demand for liquid at these diffusion operation levels and cartridges will have to be changed more often to maintain these levels of treatment. It is anticipated that these control schemes are to be used only in special circumstances and will not be commonly used control schemes.

Figure 5:
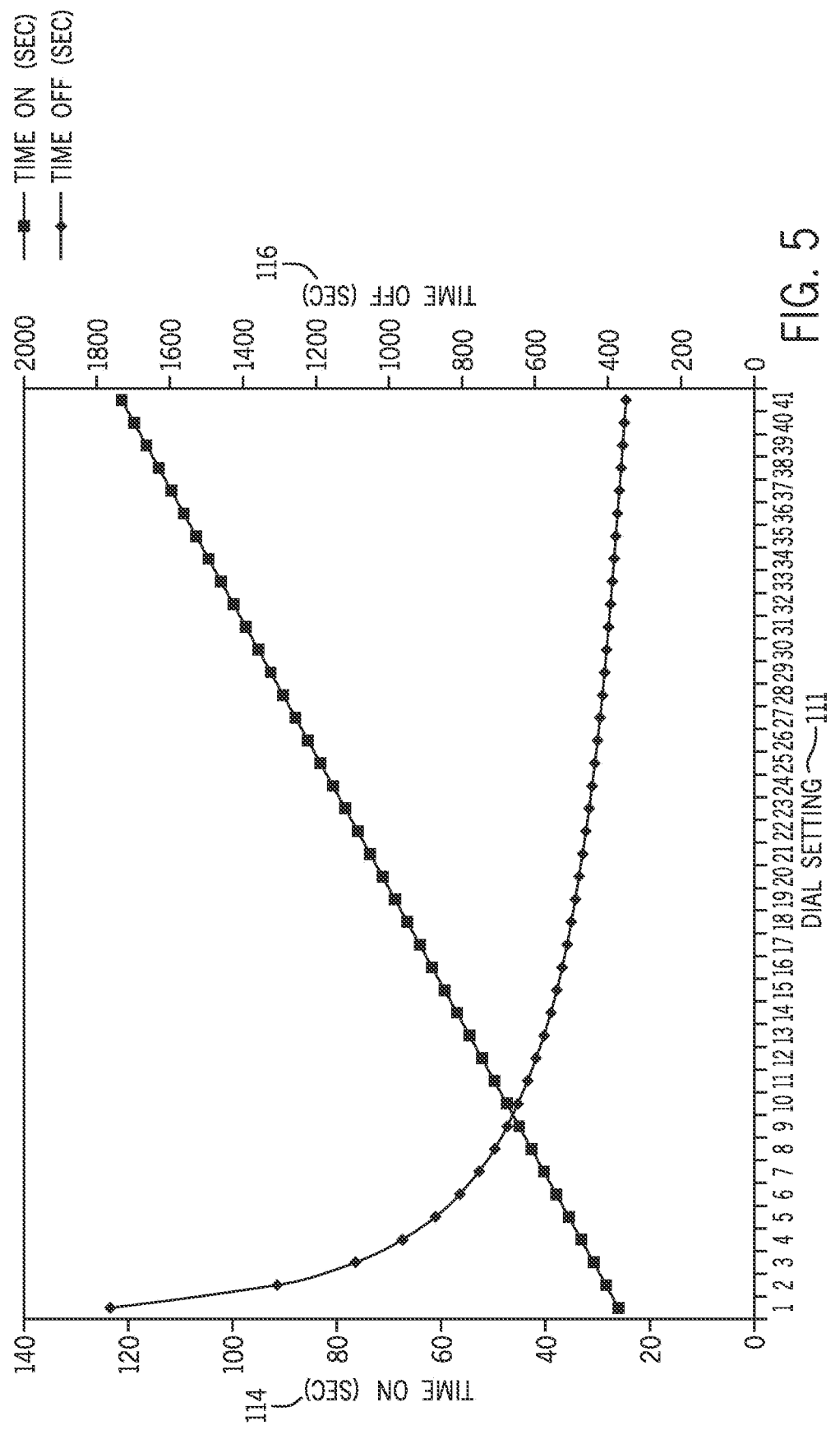
FIG. 5 is a chart illustrating the time cycle between time on and time off of the control schemes of FIG. 4.

FIGS. 5 to 8 include charts to illustrate different characteristics of control schemes 110 of the chart of FIG. 4. FIG. 5 shows in graphical form the amount of time on duration and the amount of time off duration for each of the settings of the chart of FIG. 4. Corresponding to the discussion above, the settings beyond 41 are not shown as those settings 42 to 47 correspond to fully on operation with varying flow levels.

Figure 6:
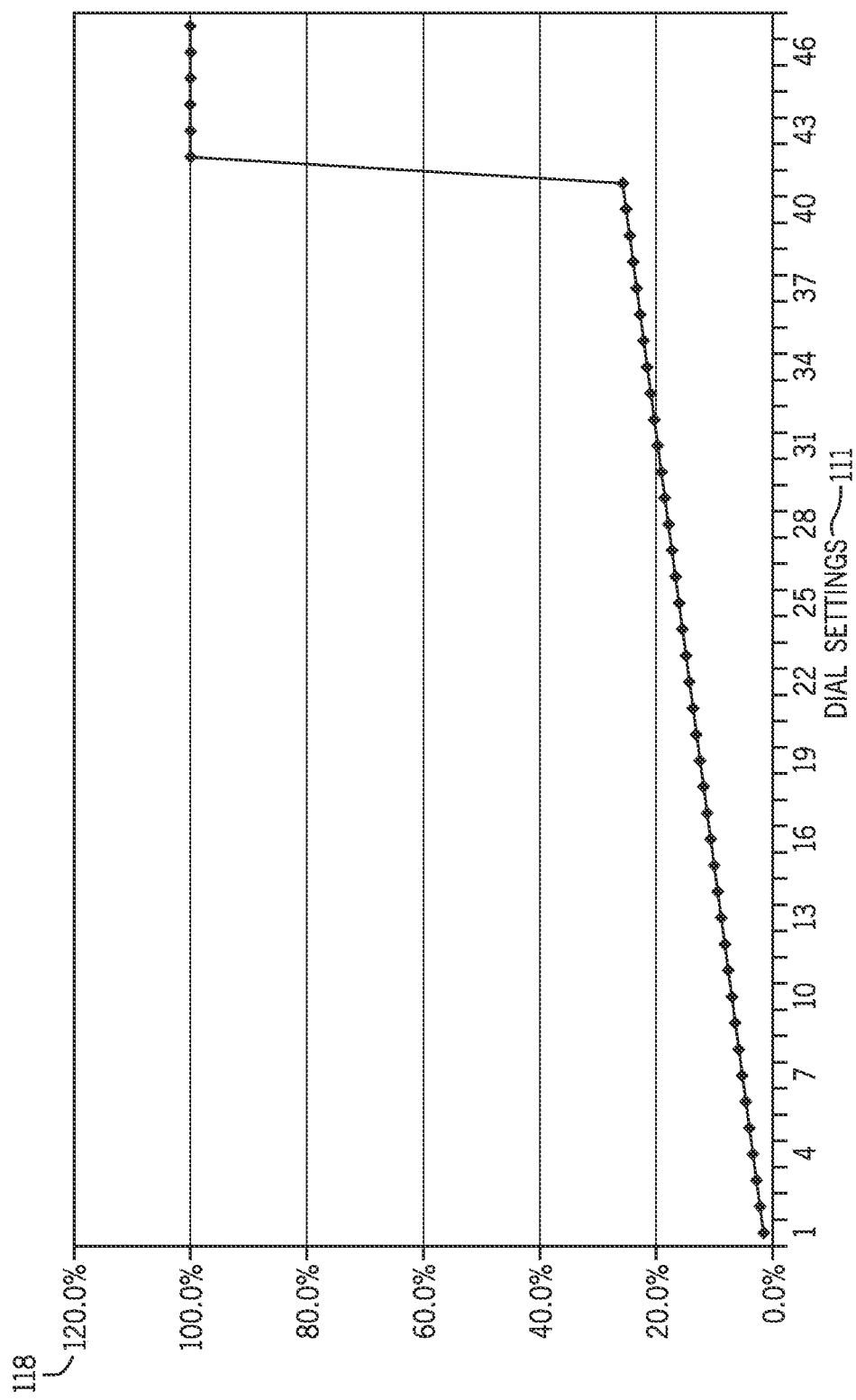
FIG. 6 is a chart illustrating the calculated duty cycle of the control schemes of FIG. 4.
Figure 7:
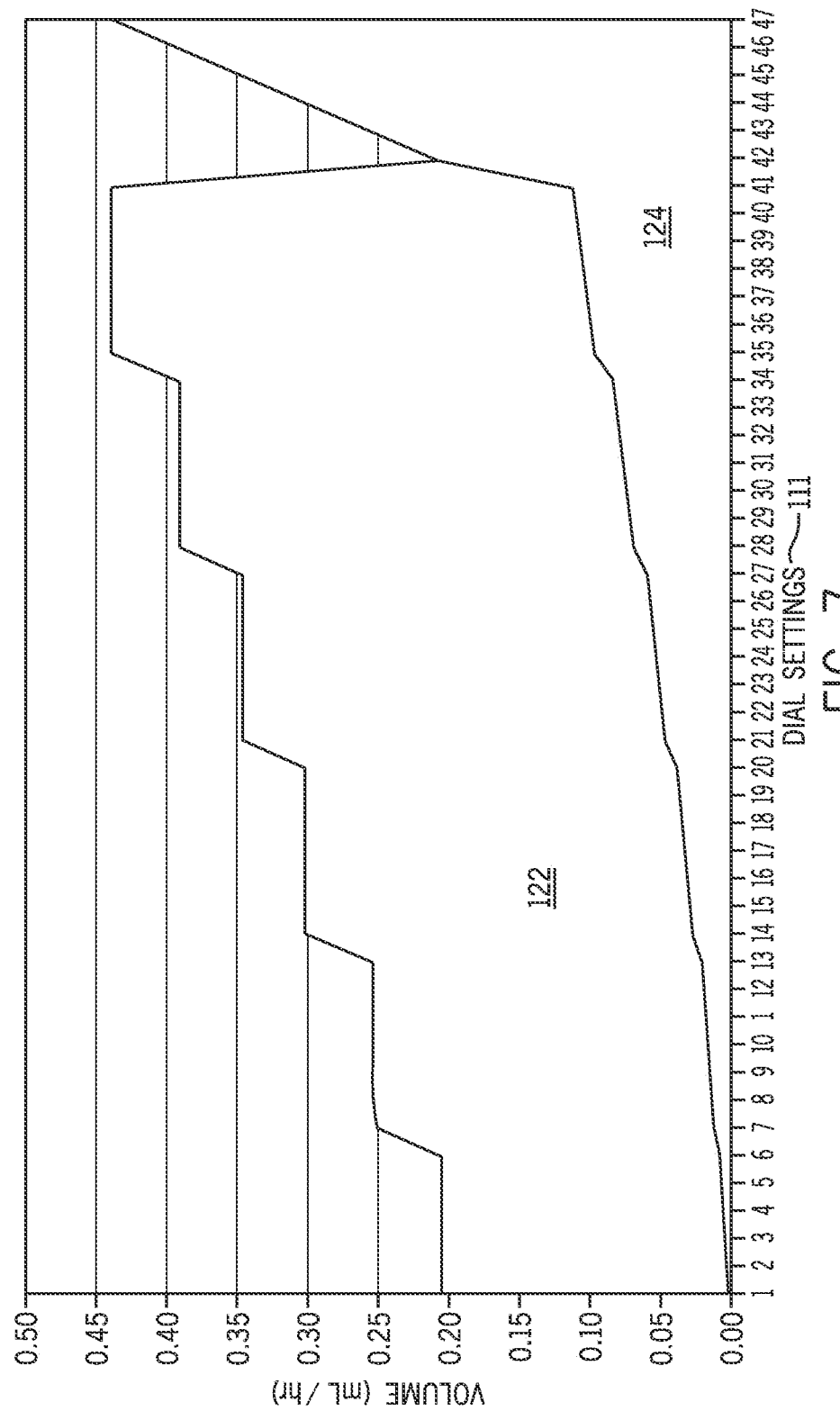
FIG. 7 is a chart illustrating the liquid output of an appliance operating under the control schemes of FIG. 4.
Figure 8:
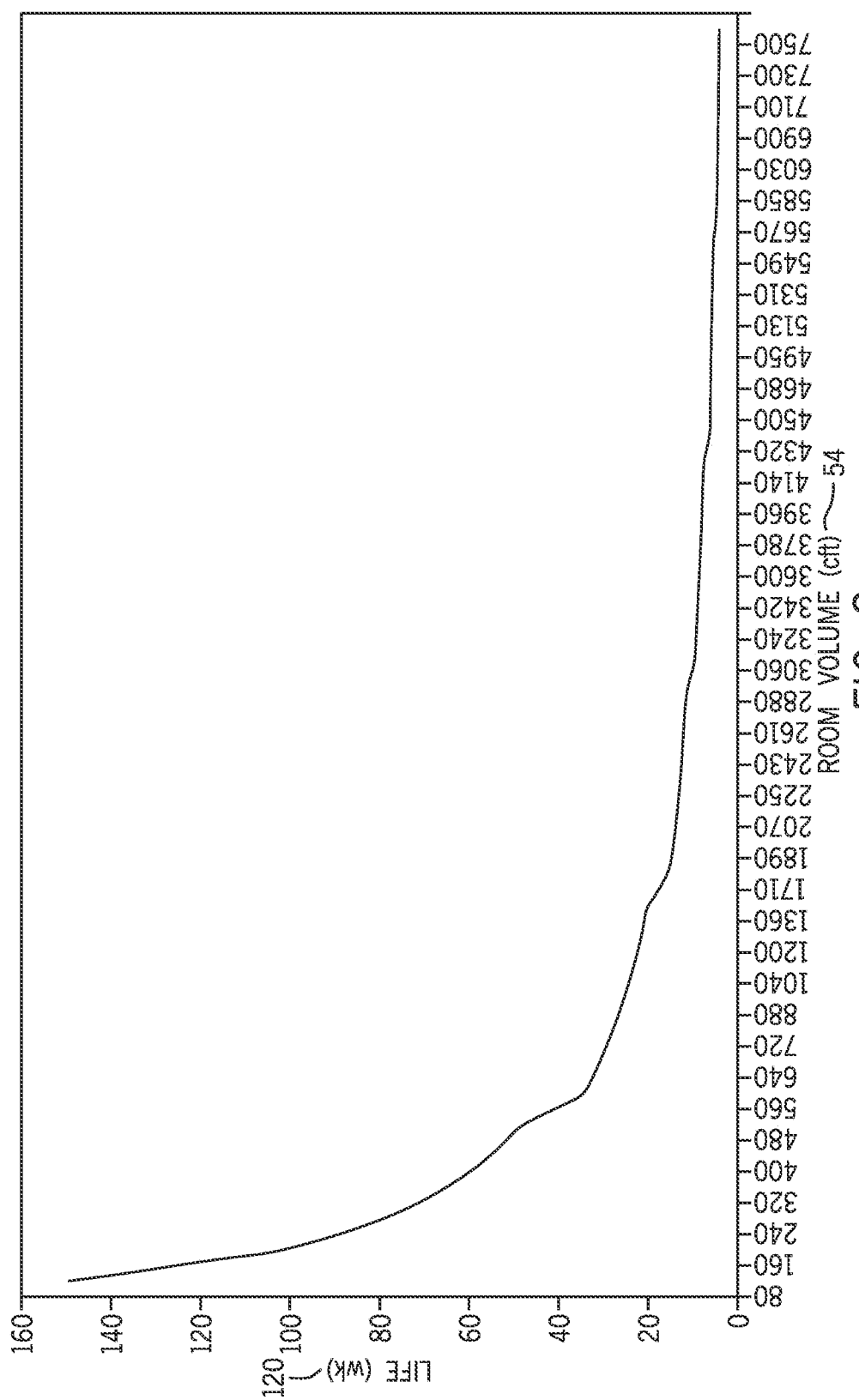
FIG. 8 is a chart illustrating the expected cartridge life for an appliance operating under the controls schemes of FIG. 4.

FIG. 6 illustrates the duty cycle derived from the time on and time off values of FIGS. 4 and 5, and shows the duty cycle of settings 42 to 47 as 100%. FIG. 7 illustrates a continuous flow rate 122 for each setting 111 and a corresponding average output 124, taking into account the flow rate 122 and the duty cycle 118 for each setting. FIG. 8 illustrates the impact that each setting will have upon the expected life 120 of a cartridge 104 used in appliance 100 and operating in accordance with one of the control schemes 110.

The relationships and graphs illustrated in FIGS. 4 to 8 relate to a particular appliance 100 with a particular cartridge 102 having a particular capacity and containing liquid 104 having common diffusion characteristics. The parameters for each setting may be changed or adapted to accommodate desired flow rates or treatment characteristics, or to accommodate different sizes of configurations of spaces to be treated. The numbers associated with each setting are intended to be illustrative only and are not intended to limit the present disclosure to any particular configuration or appliance or space or parameters of operation.

When treatment of the atmosphere within a space is initiated, it may be desirable to provide a more rapid buildup to a desired level or concentration of treatment and then have the appliance transition into a steady-state or maintenance operation. There may be several approaches to accomplishing this sort of rapid buildup within the scope of the present disclosure. One of these approaches is to provide for a 100% duty cycle operation for a set period of time to be associated with each of the control schemes. As each control scheme is designated for a particular volume or shape of space, the duration of the 100% duty cycle for each setting could be selected to correspond to that particular space while maintaining the flow rate specified for the associated control scheme. Upon completion of the initiation phase, the appliance would switch to functioning according to the selected control scheme. Similarly, instead of a 100% duty cycle, an increased duty cycle of greater than that specified for a control setting but less than 100% may be used in the initiation phase for that control scheme.

Alternatively, the duty cycle of the setting could be maintained and the control scheme could be associated with a greater flow rate during the initiation phase. For example, referring to FIG. 4, setting 5 might increase the flow rate from 40% to 65% during initiation. After initiation, the flow rate could be reduced to the 40% normally specified for the control scheme associated with setting 5.

Some combination of flow rate and duty cycle enhancement may also be used to define an initiation phase, and the initiation phase associated with different control schemes may have different approaches to the use of increased duty cycle or increased flow rate or the combination thereof.

As a further alternative, as shown in FIG. 1, one or more atmospheric sensors 70 may be included within space 50 and may be used to determine when to exit the initiation phase and move to operation under the selected control scheme for space 50. In such a configuration, instead of having the initiation phase extend for a set period of time, the initiation phase can be ended when the desired amount of concentration of liquid is in the atmosphere of the space. Of course, a combination of sensing a concentration and operation in the initiation phase for a set period of time may be used as well. Sensor(s) 70 can be used to override/adjust operational parameters of appliance 52. Different types of sensors 70 can be used as well. By way of example and not limited to these, a sensor 70 may be used which detects the concentration of one or more of the chemical components of the liquid or a different sensor 70 may measure carbon dioxide within space 50 as a way of estimating the number of people in the room. The outputs of such sensors may then be used to alter the operational parameters of the appliance to address the situation within space 50. Different levels of activity within the same space may demand operational parameters different from those based on a predetermined average level of activity within the space.

Sensors 70 may be used to alter the operation of appliance 52 based on the conditions within space 50. The alteration to the operation may be to select a different control scheme where the first control scheme used is selected based on the size of the space and the second control scheme is selected based also on the activity within the space. As noted above, the sensor may be used to determine when to transition from a start-up mode of operation to operation under one of the other control schemes. The sensor may be used to determine when an anti-fatigue scheme has achieved the desired alteration of the level of treatment within the space and thus when to return to operation of the appliance according to a different control scheme.

It is further anticipated that controller 106 may be connected to a sensor within the space to be treated and that the sensor may be configured to sense the level of the liquid dispersed within the air in the space. While the present disclosure may utilize standardized tables to determine operational parameters, it is anticipated that the present disclosure may include a sensor adjustment loop as well, so that the operational parameters of the device may be altered based on a variation of the atmospheric conditions within the space. For example, as humidity within the space varies, the dispersion of the liquid within the space and the saturation point for the liquid within the space may vary from assumed parameters used to develop the tables described above. Sensors capable of detecting the level of scent-inducing compounds within the air in the space may be used to alter the amount of timing of the release of scent compounds to maintain a desired level of scenting within the space. Further, scent sensors may be adapted to sense the presence of noxious, irritating or otherwise unpleasant odors within the space to be treated and signal the controller to operate the device of the present disclosure to remediate these undesirable odors.

Figure 9:
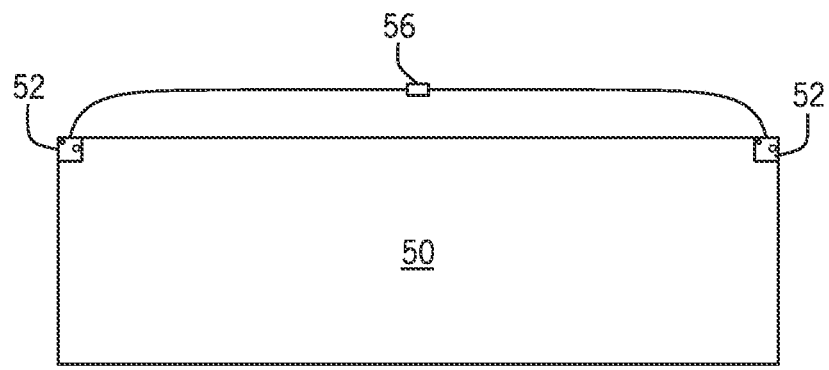
FIG. 9 is a schematic diagram of an enclosed space including a plurality of liquid diffusion appliances according to the present disclosure.

As shown in FIG. 9, a plurality of appliances 52 may be used to treat space 50 and the individual appliances could be controlled centrally for coordinated operation by a central controller 56. Alternatively, each of the appliances could be controlled by a local or dedicated controller, such as controller 106, and operate independently from the other appliances treating the same space. Central controller 56, or individual controllers 106, may operate the connected appliance(s) 52 according to control schemes and variations described herein. As a further alternative, one or a plurality of sensors 70 may be used to alter the operation of the appliances 52 from the control schemes, as described herein. Thus, larger or irregularly shaped spaces, or spaces which may have varying amounts of air exchange or activity generating the need for treatment in different areas, can be effectively and efficiently treated using appliances according to the present disclosure.

Figure 10:
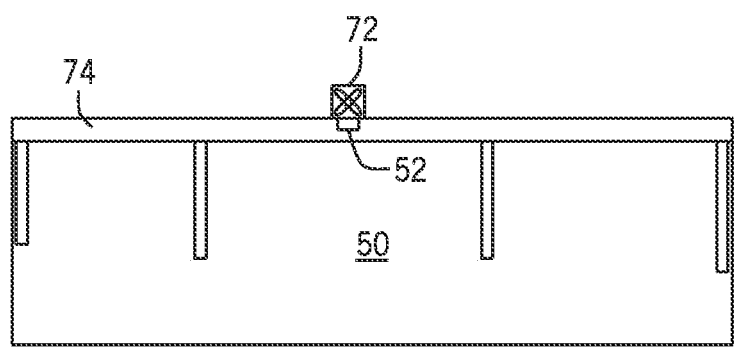
FIG. 10 is a schematic diagram of an enclosed space with air distribution ductwork and a liquid diffusion appliance according to the present disclosure mounted in the ductwork.
Figure 11:
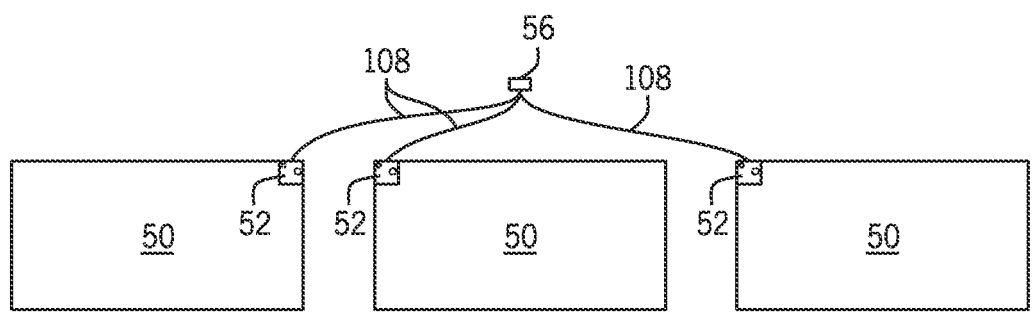
FIG. 11 is a schematic diagram of a plurality of enclosed spaces, each with a liquid diffusion appliance according to the present disclosure.

Because appliances such as appliance 52 may be used to treat larger spaces, it may be desirable to have an auxiliary fan to aid in the distribution of the liquid diffused by the appliance throughout the space 50. An example of an auxiliary fan 72 for aiding distribution may be a HVAC fan that is part of a forced air heating or cooling installation, such as shown in FIG. 10. Appliance 52 may be positioned within or positioned to diffuse liquid into a supply duct 74 of such an installation and the diffused liquid may be dispersed throughout space 50 whenever fan 72 is operating. In this type of installation, the operation of the auxiliary fan may not be controlled by or dependent on the operation of the appliance.

Alternatively, as shown in FIG. 1, appliance 52 may be installed adjacent a dedicated auxiliary fan 72 to aid in the dispersal of the diffused liquid. In this alternative installation or configuration, auxiliary fan 72 may be controlled in conjunction with the operation of the appliance. Thus, auxiliary fan 72 would only be operated in coordination with liquid diffusion. Auxiliary fan 72 may operate simultaneously with the appliance, may be offset to come on after diffusion has begun and stay after diffusion has been completed for the on portion of the control scheme, or operated in some other arrangement relative to the on portion of the control scheme.

A plurality of appliances 52 may be positioned to each treat a plurality of similarly sized and/or configured spaces, such as banquet rooms, meeting rooms, offices, hotel rooms, etc., such as shown in FIG. 11. For treatment of such similar spaces 50, central controller 54 could be used to operate all of the appliances 52 jointly. As an example, these appliances could be connected to a common compressed gas supply 108 and central controller 56 could operate the supply to control diffusion of the liquid from each appliance simultaneously. Or, each appliance 52 could include an independent source of compressed gas, such as an on-board compressor, and central controller 54 could control the supply of power to each of the compressors to control diffusion. In addition, each of these appliances 52 could be located with respect to an auxiliary fan 72 to aid in the dispersion of the liquid being diffused by each appliance.

People who are in the space being treated may become less sensitive to the treatment in the atmosphere of the space or may be fatigued and no longer notice the treatment. This is a common phenomenon, particularly with regard to scents or aromas used to treat the atmosphere, and it may be desirable to provide some degree of variability in the concentration of liquid 104 in the atmosphere. Variations in the concentration above and below the desired level of concentration at some intervals may be used to combat the onset of fatigue to the treatment and enhance the effectiveness of the treatment at the desired level.

In the context of the present disclosure, such anti-fatigue variations may be provided by one or more temporary alterations to the selected control scheme. A first approach might be to reduce the duty cycle to 0% for a set period of time, so that the concentration with the space is allowed to drop below the desired level. At the end of this time, the duty cycle may be returned to the specified value for the control scheme and the concentration allowed to build back to the desired level. Similarly, while decreases in concentration may be more desirable or effective in combating fatigue, the duty cycle might be increased for a period of time above the duty cycle specified for the control scheme to provide an increased concentration in the space. After the period of time, the duty cycle may be reduced to the specified duty cycle of the control scheme and the concentration in the space permitted to return to the desired level.

Alternatively, the flow rate could be reduced below the flow rate of the control scheme to reduce the concentration in the space, or increased above the flow rate of the control scheme to increase the concentration in the space. The alterations to flow rate could be maintained for a period of time and then allowed to return to the flow rate specified for the selected control scheme. A combination of variation of flow rate and duty cycle may be used to accomplish the variation in concentration with the space.

The interval between anti-fatigue variations in the operation of the appliance may be fixed by a particular anti-fatigue scheme, or may be randomly variable. A particular anti-fatigue variation scheme may be associated with each control scheme setting of the appliance or a common anti-fatigue variation scheme may be incorporated for use with all settings of the appliance. A fixed anti-fatigue scheme may include variation of the flow rate at certain predetermined intervals, variation in operation of the diffusion means at certain predetermined intervals, or a combination of varying the two parameters according to predetermined patterns. Alternatively, the variation of flow rate and/or operation may be completely on a random basis, with all parameters subject to variation according to a random scheme. This random anti-fatigue scheme may be governed by certain constraints to ensure that the concentration within the space does not exceed or go below certain desired levels.

It should be noted that the periodic operation of the diffusion means within the control schemes according to the present disclosure provide a degree of anti-fatigue function. The periodic operation of the diffusion means will provide at least some degree of variation in the concentration of liquid 104 within space 50 and this variability may reduce the need or desirability of having a more distinct variation as might be created by an anti-fatigue scheme according to the present disclosure.

As mentioned above, use of pauses or periods of non-operation within the control schemes may provide variation on the concentration of liquid within a space that may aid in the avoidance or reduction of fatigue or adaptation. A length of pause may be selected to permit sufficient decay to occur to drop the concentration to a lower level with the space. When the pause is ended, the operation of appliance 100 brings the concentration back up to a higher level. Thus, the pauses inherent in the duty cycle may be used to provide an anti-fatigue effect as well. Even with the same specified duty cycle, the length of each pause may be tailored to permit a greater or lesser degree of decay and thus reduction of concentration. For example, a 25% duty cycle may have pauses of three minutes and operation times of one minute. The same device programmed with pauses of forty-five minutes and operation times of fifteen minutes will have the same calculated duty cycle but will permit a greater degree of concentration variation within the space to the be treated. The length of pause may be selected based on the nature of the liquid being diffused, the number and/or area of surfaces into which particles within the space may contact, and the rate of atmospheric turnover within the space.

Much of the above discussion has suggested a longer term operation of appliance 100 to provide a particular level or concentration of liquid 104 within the atmosphere of the space. However, it is anticipated that appliance 100 could also be configured to operate according to a control scheme for a more discrete period of time or initiated on demand. The operation of appliance 100 might be initiated in reaction to an event within the space and only operate for the expected duration needed to respond to the event. For example, if space 50 is a hotel lobby, and liquid 104 is a disinfecting agent, appliance 100 may be configured to function in the early morning hours to provide an effective concentration of liquid 104 within space 50. This may be the time of least movement through the space and may ensure the most uniform treatment of the atmosphere and surfaces within the space. Treatment during the day or in times of heavy traffic may not be as desirable or effective. Alternatively, appliance 100 may be used to place a concentration of a scent into a meeting room space in anticipation of a scheduled meeting but may not need operate during the meeting.

Much of the discussion above has been directed to altering both the parameters relating to duty cycle and flow rate to adjust the output of the device of the present disclosure to match the space to be treated as well as the atmospheric conditions within that space. It has been determined that a plurality of control schemes where the flow rate of the device is kept constant and the alteration of the amount of liquid dispersed is controlled by altering the duty cycle may be the preferred approach. Such a control pattern may be simpler to implement and allow more effective control of the dispersion of liquid into a space to be treated. It is not intended to limit the present disclosure to such a single variable approach to control schemes but operational experience with devices according to the present disclosure indicates that this may be a preferable approach.

It should be noted within the scope of the present disclosure that a variety of functions may be accomplished through the use of the devices and control schemes of the present disclosure to disperse liquids within a space. Beyond scenting of the air with a specific scent for a desired effect, the treatment of the air within a space may be to remediate odors within the space or to control or neutralize a particular known odor that may be constantly or periodically present within the space. Device and control schemes according to the present disclosure may be used to disperse pest control liquids within the space. Such liquids may include but are not limited to bird or other animal repellents and pesticides. One non-limiting example of a use of a device according to the present disclosure is the use of the device to disperse compounds which are irritating or noxious to various species of birds that may invade or take up residence in aircraft hangars. Similarly, anti-rodent compounds may be dispersed within food storage or preparation facilities.

It is anticipated that the device of the present disclosure may be used to disperse anti-microbials or other compounds which may remediate environmental pathogens within the space. Such pathogens may be naturally occurring and may be the result of a natural infestation of exposure within the space. Alternatively, the pathogens may have been deliberately introduced within the space, such as but not limited to weaponized pathogens. The device of the present disclosure may be used to provide a persistent treatment to guard against the introduction of pathogens, such as but not limited to health care spaces, but also may be used to remediate a biological attack. As a non-limiting example, the device and control schemes of the present disclosure might have been useful to disperse an anti-anthrax agent within various government office buildings that were targeted by biological attacks following the World Trade Center attacks.

While the invention has been described with reference to preferred embodiments, it is to be understood that the invention is not intended to be limited to the specific embodiments set forth above. Thus, it is recognized that those skilled in the art will appreciate that certain substitutions, alterations, modifications, and omissions may be made without departing from the spirit or intent of the invention. Accordingly, the foregoing description is meant to be exemplary only, the invention is to be taken as including all reasonable equivalents to the subject matter of the invention, and should not limit the scope of the invention set forth in the following claims.

The invention claimed is:

1. A method of maintaining a desired level of a dispersed liquid within an occupiable semi-enclosed space having entrances and exits subjected to entry and exit of occupants to and from the occupiable semi-enclosed space, the method comprising:
   providing a liquid diffusion appliance including a liquid to be dispersed and including a controller for operating the liquid diffusion appliance to disperse the liquid into the air within the occupiable semi-enclosed space to be treated, the controller of the liquid diffusion appliance being communicatively coupled to a sensor in fluid communication with the air within the occupiable semi-enclosed space to be treated, and the sensor being configured to sense the concentration of one or more chemical components of the dispersed liquid within the occupiable semi-enclosed space to be treated;
   operating the liquid diffusion appliance to disperse the liquid into the occupiable semi-enclosed space throughout a treatment period in which the occupiable space is subjected to entry and exit of occupants to and from the occupiable semi-enclosed space;
   sensing the concentration of the one or more chemical components of the dispersed liquid within the occupiable semi-enclosed space with the sensor; and modifying the operation of the liquid diffusion appliance based on the concentration of the one or more chemical components of the dispersed liquid within the occupiable semi-enclosed space to achieve a desired concentration, wherein the modifying of the operation of the liquid diffusion appliance includes modifying a flow rate of the liquid to be dispersed during at least a portion of the treatment period in which the liquid diffusion appliance is actively dispersing the liquid, wherein the modifying of the operation of the liquid diffusion appliance includes transitioning the liquid diffusion appliance from an initiation phase control scheme to a maintenance phase control scheme based on the concentration of the one or more chemical components of the dispersed liquid within the occupiable semi-enclosed space, and wherein the initiation phase control scheme is associated with a relatively higher flow rate of the liquid to be dispersed than the maintenance control scheme.

2. The method of claim 1 wherein the liquid to be dispersed comprises a disinfecting agent and operating the liquid diffusion appliance to disperse the liquid into the occupiable semi-enclosed space includes dispersing the disinfecting agent into the occupiable semi-enclosed space.

3. The method of claim 1, further comprising:
sensing a number of occupants in the occupiable semi-enclosed space to be treated; and
altering the operation of the diffusion device based on the number of occupants.

4. The method of claim 1 wherein a cartridge containing the liquid to be dispersed is accommodated in the liquid diffusion appliance, and wherein operating the liquid diffusion appliance to disperse the liquid into the occupiable semi-enclosed includes moving pressurized gas through a venturi to withdraw liquid from the cartridge and to disperse the liquid into the occupiable semi-enclosed space via an outlet of the liquid diffusion appliance.

5. The method of claim 4 wherein modifying the operation of the liquid diffusion appliance includes adjusting a rate of gas passed through the venturi.

6. The method of claim 1, further comprising:
operating an auxiliary fan to aid in the distribution of the liquid dispersed by the liquid diffusion appliance during the treatment period.

7. The method of claim 1 wherein the liquid diffusion appliance is one of a plurality of liquid diffusion appliances, and wherein operating the liquid diffusion appliance to disperse the liquid into the occupiable semi-enclosed space throughout the treatment period includes operating each of the plurality of liquid diffusion appliances in a coordinated manner to achieve the desired concentration of the one or more chemical components of the dispersed liquid within the occupiable semi-enclosed space.

8. A liquid diffusion system for treating an occupiable semi-enclosed space with a dispersed liquid, the liquid diffusion system comprising:
a liquid diffusion appliance including the liquid to be dispersed;

a controller for operating the liquid diffusion appliance to disperse the liquid into the occupiable semi-enclosed space to be treated; and a sensor in fluid communication with the air in the occupiable semi-enclosed space to be treated and communicatively coupled to the controller, the sensor configured to sense the concentration of one or more chemical components of the dispersed liquid within the occupiable semi-enclosed space to be treated throughout a treatment period in which the occupiable semi-enclosed space is subjected to entry and exit of occupants to and from the occupiable semi-enclosed space, and wherein the controller is configured to modify a flow rate of the liquid to be dispersed during at least a portion of the treatment period in which the liquid diffusion appliance is actively dispersing the liquid based on the concentration of the one or more chemical components of the dispersed liquid within the occupiable semi-enclosed space to be treated, wherein the controller is configured to transition the liquid diffusion appliance from an initiation phase control scheme to a maintenance phase control scheme based on the concentration of the one or more chemical components of the dispersed liquid within the occupiable semi-enclosed space, and wherein the initiation phase control scheme is associated with a relatively higher flow rate of the liquid to be dispersed than the maintenance control scheme.

9. The liquid diffusion system of claim 8, further comprising:
at least one additional sensor that is configured to sense a number of occupants within the occupiable semi-enclosed space to be treated, and
wherein the controller is further configured to modify the operation of the liquid diffusion appliance based at least in part on said number of occupants.

10. The liquid diffusion system of claim 8, further comprising:
an auxiliary fan to aid in the distribution of the liquid dispersed by the liquid diffusion appliance throughout the occupiable semi-enclosed space.

11. The liquid diffusion system of claim 8 wherein the controller and the sensor provide a sensor adjustment loop for altering operational parameters of the liquid diffusion appliance based on a variation of atmospheric conditions within the occupiable semi-enclosed space to be treated.

12. The liquid diffusion system of claim 8 wherein the liquid diffusion appliance is one of a plurality of liquid diffusion appliances, and wherein the controller is configured to control the liquid diffusion appliances in a coordinated manner to achieve a desired concentration of the one or more chemical components of the dispersed liquid within the occupiable semi-enclosed space.

13. The liquid diffusion system of claim 8 wherein the liquid diffusion appliance includes a cartridge containing the liquid to be dispersed and a venturi through which gas is passed to withdraw liquid from the cartridge for dispersion into the occupiable semi-enclosed space.

* * * * *